United States Patent [19]

Mann et al.

[11] Patent Number: 4,790,647
[45] Date of Patent: Dec. 13, 1988

[54] EXAMINATION UNIT

[75] Inventors: Dieter Mann, Aschaffenburg; Dieter Fornoff, Darmstadt; Andreas Ries, Darmstadt; Eberhard Klett, Darmstadt; Michael van Suntum, Darmstadt, all of Fed. Rep. of Germany

[73] Assignee: Dieter Mann GmbH, Aschaffenburg, Fed. Rep. of Germany

[21] Appl. No.: 805,854

[22] Filed: Dec. 5, 1985

[30] Foreign Application Priority Data

Dec. 6, 1984 [DE] Fed. Rep. of Germany ....... 3444580

[51] Int. Cl.[4] .............................................. A61B 3/00
[52] U.S. Cl. ................................................. 351/245
[58] Field of Search ....................... 351/245, 246, 244; 312/209

[56] References Cited

U.S. PATENT DOCUMENTS

| 1,651,661 | 12/1927 | Armbruster | 351/245 |
|---|---|---|---|
| 3,201,795 | 8/1965 | Cüppers et al. | 351/245 |
| 3,263,627 | 8/1966 | Russell, Sr. | 351/245 |
| 3,572,913 | 3/1971 | Korb | 351/245 |
| 3,594,072 | 7/1971 | Feather | 351/245 |
| 3,891,311 | 6/1975 | Fletcher et al. | 351/245 |
| 3,929,309 | 12/1975 | De Vore | 351/245 |
| 4,094,593 | 6/1978 | Kutscherauer et al. | 351/245 |
| 4,095,379 | 6/1978 | Weintraub | 52/29 |
| 4,643,547 | 2/1987 | Collins et al. | 351/245 |

FOREIGN PATENT DOCUMENTS

| 1086457 | 8/1960 | Fed. Rep. of Germany | 351/245 |
|---|---|---|---|
| 1220082 | 6/1966 | Fed. Rep. of Germany | 351/245 |
| 265700 | 10/1968 | Fed. Rep. of Germany | |
| 1300360 | 7/1969 | Fed. Rep. of Germany | 351/245 |
| 1487569 | 5/1967 | France | 351/245 |
| 2402438 | 4/1979 | France | |
| 483827 | 2/1970 | Switzerland | 351/245 |

OTHER PUBLICATIONS

*Die Neugestaltung der Spaltlampe*, (The Redesign of the Slit Lamp), Feb. 1961, thesis for High School for Zeiss advertisement, British Journal of Ophthamology, Jun. 1972, p. 17.
*A Prospectus of Rodenstock Instruments GmbH*, Munich, "Opthalmologische Gerate", No. 1219-5d-e/5-11.77.

Primary Examiner—Charles T. Jordan
Assistant Examiner—Michael J. Carone
Attorney, Agent, or Firm—Donald Brown; Robert T. Gammons

[57] ABSTRACT

An ophthalmologic examination unit comprises a chin rest (31) and a plurality of examination instruments (30, 59, 60) whose position can be laterally adjusted relative to the patient's eyes to be examined and which can be adjusted in elevation. The chin rest (31) and the instruments (30, 59, 60) are attached to a common supporting element (13) which can be vertically adjusted by means of a drive unit (18), such that the examination procedure be rendered as simple and convenient as possible and that the instrument setting be facilitated.

13 Claims, 5 Drawing Sheets

EXAMINATION UNIT

The invention relates to an ophthalmologic examination unit, comprising a chin rest and a plurality of examination instruments whose position can be laterally adjusted relative to the patient's eyes to be examined and which can be vertically adjusted.

It is known in such ophthalmologic examination units to arrange the individual examination instruments on respective swing-out tables which are swung through a swivel arm from a lateral support into the examination range between the patient and the ophthalmologist. The individual swing-out tables are vertically fastened to the support while each instrument is individually adjusted in elevation.

It is the object of the invention to provide an improved ophthalmologic examination unit. It is a further object of the invention to render the examination procedure less complicated and more convenient, and specifically to simplify the adjustment of the instruments to patients of different sizes. It is a still further object to invention to simplify the mode of accounting at the same time.

This object is achieved by an ophthalmologic examination unit of the type described by way of introduction, which, according to the invention, is characterized in that the chin rest and the instruments are attached to a common supporting element, and that a first drive unit is provided for vertical adjustment of the supporting element.

Further features of the invention are characterized in the dependent claims.

Further features and characteristics of the invention result form the description of an embodiment of the invention with reference to the Figures. In the Figures FIG. 1 is a perspective view of one embodiment of the examination unit according to the invention;

Figure 1:
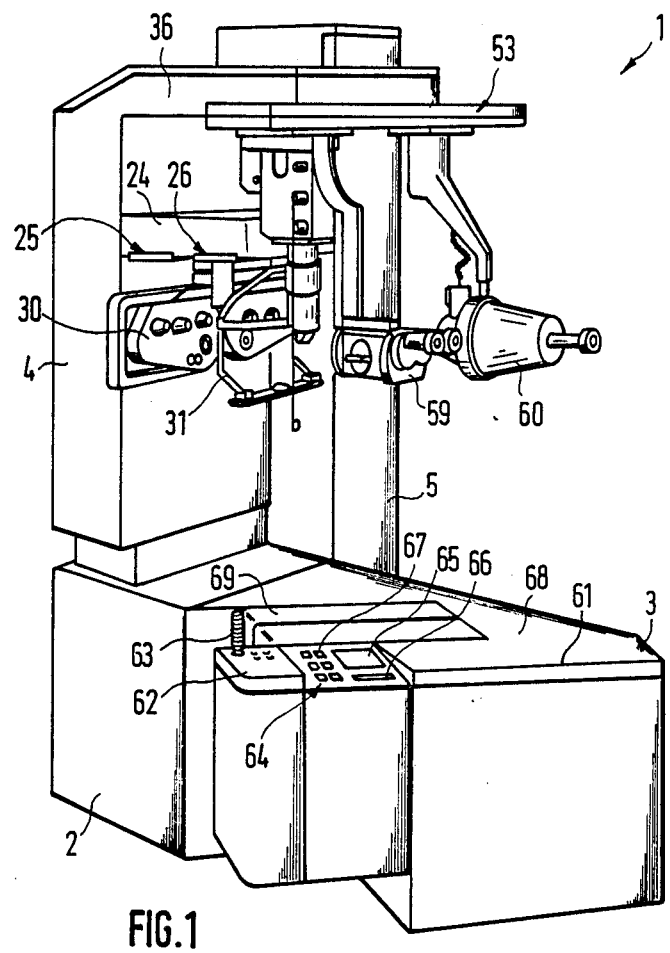

FIG. 1 is a perspective view of one embodiment in a modular design of the inventive examination unit 1. It comprises a box-type base element 2 approximately as high as a table, a control element 3 joining the front side of the base element 2, an instrument assembly 4 arranged on said base element 2, which carries the attached individual examination instruments, as well as a column-type element 5 arranged laterally of said base element 2 and said instrument assembly 4. The arrangements, the structures and the functions of the individual elements and assemblies will be described in more detail hereinbelow.

Figure 2:
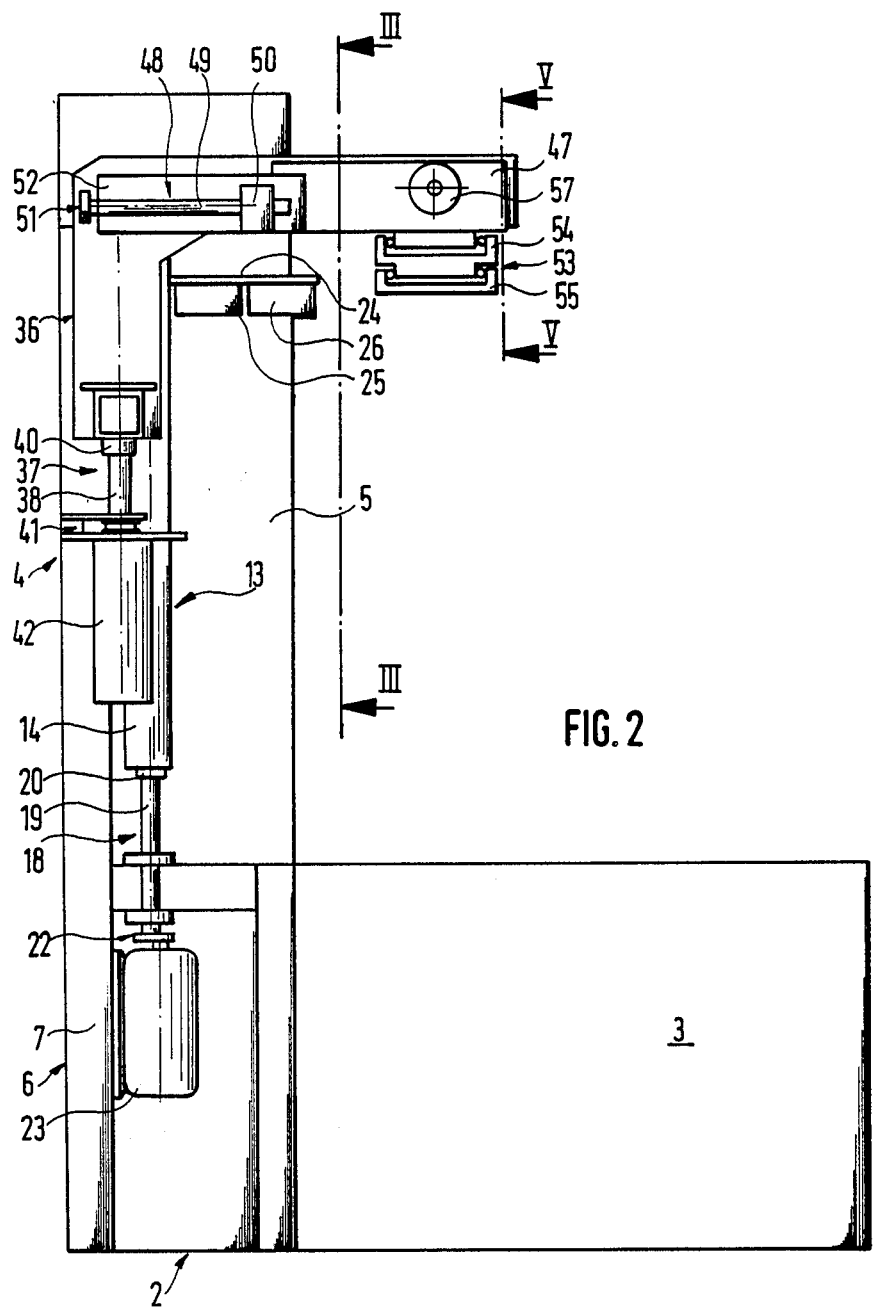
FIG. 2 is a schematic side view of the inventive examination unit according to FIG. 1, with the lateral paneling being removed.
Figure 3:
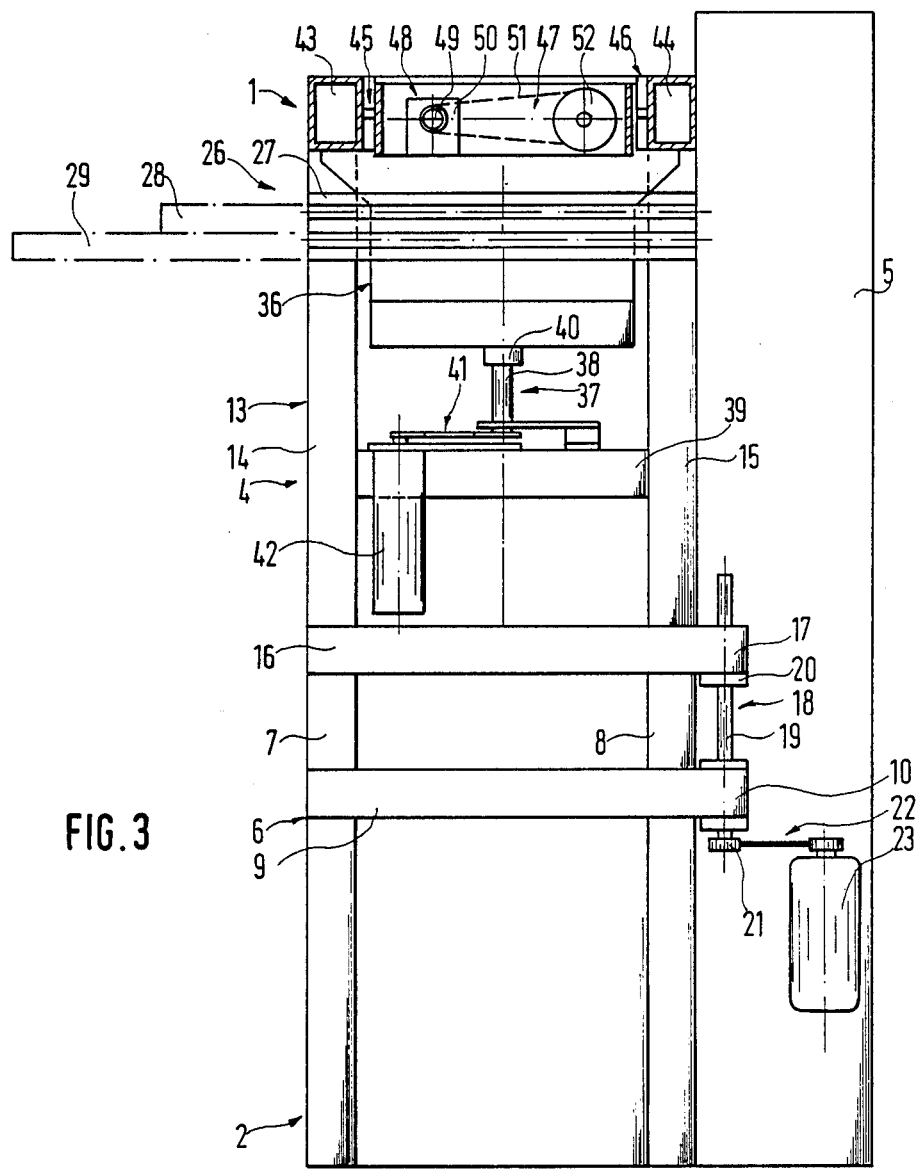
FIG. 3 is a sectional view of the inventive examination unit according to FIG. 1, taken along the line III—III in FIG. 2.

As is shown in particular in FIGS. 2 and 3, a supporting frame 6 is provided in the base element 2 and the instrument assembly 4 on their rear sides turned away from the viewer in FIG. 1, said supporting frame 6 comprising two substantially vertical frame elements 7, 8 and a horizontal crossbar 9 connecting said element approximately at the elevation of a table; this crossbar is provided with an area 10 projecting beyond the frame element 8 on its side facing the column element 5. Longitudinal guides 11, 12, for instance in the form of ball or roller guides, are provided at the frame elements 7, 8 in the manner shown in FIG. 4 in their areas above the crossbar 9; a supporting element in the form of a mobile frame 13 is arranged at these guides for vertical displacement. The frame 13 is provided with two stringers 14, 15 arranged with a spacing corresponding to the mutual spacing of the frame elements 7, 8, as well as with a substantially horizontal crossbar 16 at their lower side, which—like the crossbar 9—is provided with a cantilever section 17 on the side facing the column element 5. A drive unit 18 is provided for the vertical displacement of the mobile frame 13. This drive unit is provided with a spindle 19 supported for rotation in the area 10 of the crossbar 9, whose threading engages in a spindle nut attached at the section 17 of the crossbar 16. The end of the spindle 19, which is turned away from the mobile frame 13, carries a pulley 21 which is connected to a driving motor 23 through a belt drive assembly 22.

On the side of the mobile frame 13, which is turned away from the supporting frame 6, a bracket 24 is attached to the frame, which carries two telescopic supports 25, 26 in parallel arrangement on its substantially horizontal bottom side. The telescopic supports are each arranged, in the manner shown in FIG. 3, for double extraction with an upper fastened rail 27, a middle mobile rail 28 guided at the fixed rail 27 approximately horizontally and laterally towards the plane of the mobile frame 13, and a lower mobile rail 29 guided at the rail 28. A phoropter 30 is suspended from the lower rail 29 of that telescopic support 25 which is arranged on the side facing the mobile frame 13, while a chin rest 31 is fastened, in suspension, too, at the lower mobile rail of that telescopic support 26 which is arranged at a greater distance from the supporting frame 13.

Figure 4:
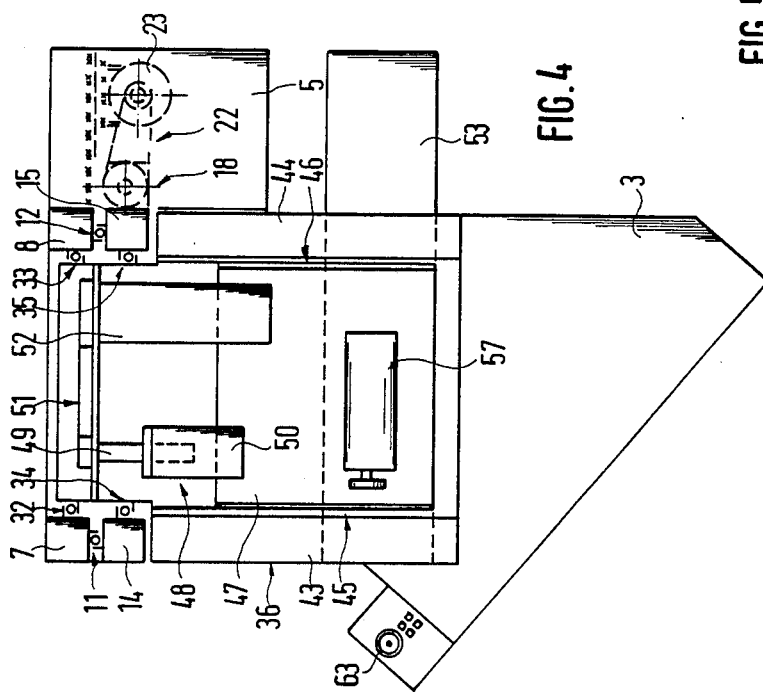
FIG. 4 is a top view of the inventive examination unit according to FIG. 1, with the top paneling being removed.

On the inner sides of the frame elements 7, 8, which respectively face each other, and at the stringers 14, 15 respectively vertical longitudinal guides 32, 33, 34, 35 are provided in the manner shown in FIG. 4, which are designed, for instance, as roller or ball guides or even dovetail guides, at which a bracket frame 36 is guided for vertical displacement. The bracket frame 36 is thus arranged for vertical displacement relative to both the supporting frame 6 and the mobile frame 13. A displacement drive 37 is provided for such displacement, whose spindle 38 is supported for rotation at a crossbar 39 fastened between the stringers 14, 15 of the mobile frame 13 and engaging in a spindle nut 40 fastened to the bottom side of the bracket frame 36. The spindle 38 is connected to a second driving motor through a belt drive assembly 41.

The bracket frame 36 is provided with two substantially horizontally projecting parallel supporting brackets 43, 44 on the frame side turned away from the supporting frame 6. These brackets are provided each with horizontal guides 45, 46 in their mutually facing inner sides, a sliding carriage 47 being provided in these guides for horizontally displacement. The horizontal displacement is achieved through a further displacement drive 48 with a spindle 49 supported in the bracket frame 36 in axially fixed and rotational relationship, while the spindle engages in a spindle nut 50 attached to the sliding carriage 47. The spindle 49 is connected for rotation to a third driving motor 52 through a belt drive assembly 51, said driving motor being fixedly arranged at the bracket frame 36.

Near its end turned away from the supporting frame 6, the sliding carriage 47 carries, at its bottom side, a telescopic bracket 53 for double extraction, similarly to the telescopic supports 25, 26. This telescopic bracket 53 is so arranged that the middle mobile rail 54 and the lower mobile rail 55 are provided for lateral displacement substantially horizontally and parallel to the supporting frame 6 in the same direction as the rails 28, 29 of the telescopic supports 25, 26. A displacement drive 56 with a fourth driving motor 57 and a belt drive assembly 58 is provided in the sliding carriage 47 for this displacement.

Figure 5:
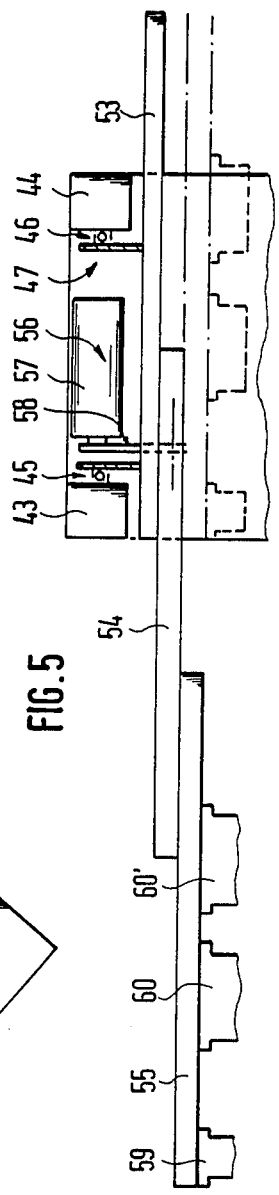
FIG. 5 is a sectional view of the inventive examination unit according to FIG. 1, taken along the line V—V in FIG. 2, with a schematic representation of laterally swung-out examination instruments.

Adjacent examination instruments 59, 60 are suspended from the bottom side of the lower mobile rail 55 in the direction of displacement of this rail. FIG. 1 shows two and FIG. 5 shows three examination instruments 59, 60, 60' in adjacent arrangement, but another number of instruments may be provided, too, whenever desired. The suspended mounting eliminates the foot which is required for each instrument in all other cases, so that the instruments may be arranged at a mutual spacing determined only by the width of each instrument. The length of the telescopic bracket 53 or the rails 54, 55 is so selected that each of the instruments 59, 60 may be moved into an examination position beside the base element 2 or the instrument assembly 4, respectively.

The column element 5 is arranged on that side of the control element 3 or the instrument assembly 4, which is opposite to this examination position; it serves to accomodate the character projector for sight testing. To this end, the projector is arranged in the upper quarter of this column element 5, which is not illustrated, and can be moved out on a rail. A rectangular cutout in the direction of the control element 3 permits the projection at a suitable elevation.

The control element 3 joins the base element 2 on the side below the examination instruments 59, 60, and is provided with a table-shaped design and a front edge 61 of the table which extends obliquely towards the examination ophthalmologist in a manner that it encloses an acute angle with the direction of the instrument (59, 60) displacement. Along the table edge, from the left to the right side as shown in FIG. 1, i.e. away from the examination place, an operating console 62 with a control switch 63, a switchboard 64 with a display 65, a card input unit 66 and other controls and operating elements such as a keyboard 67 and a desk surface 68 are provided. Moreover, behind the operating console or control board, when seen from the table edge 61, vertically withdrawable compartments or drawers 69 are provided in parallel to the table edge 61, where medicaments, glasses, etc. can be accomodated.

Figure 6:
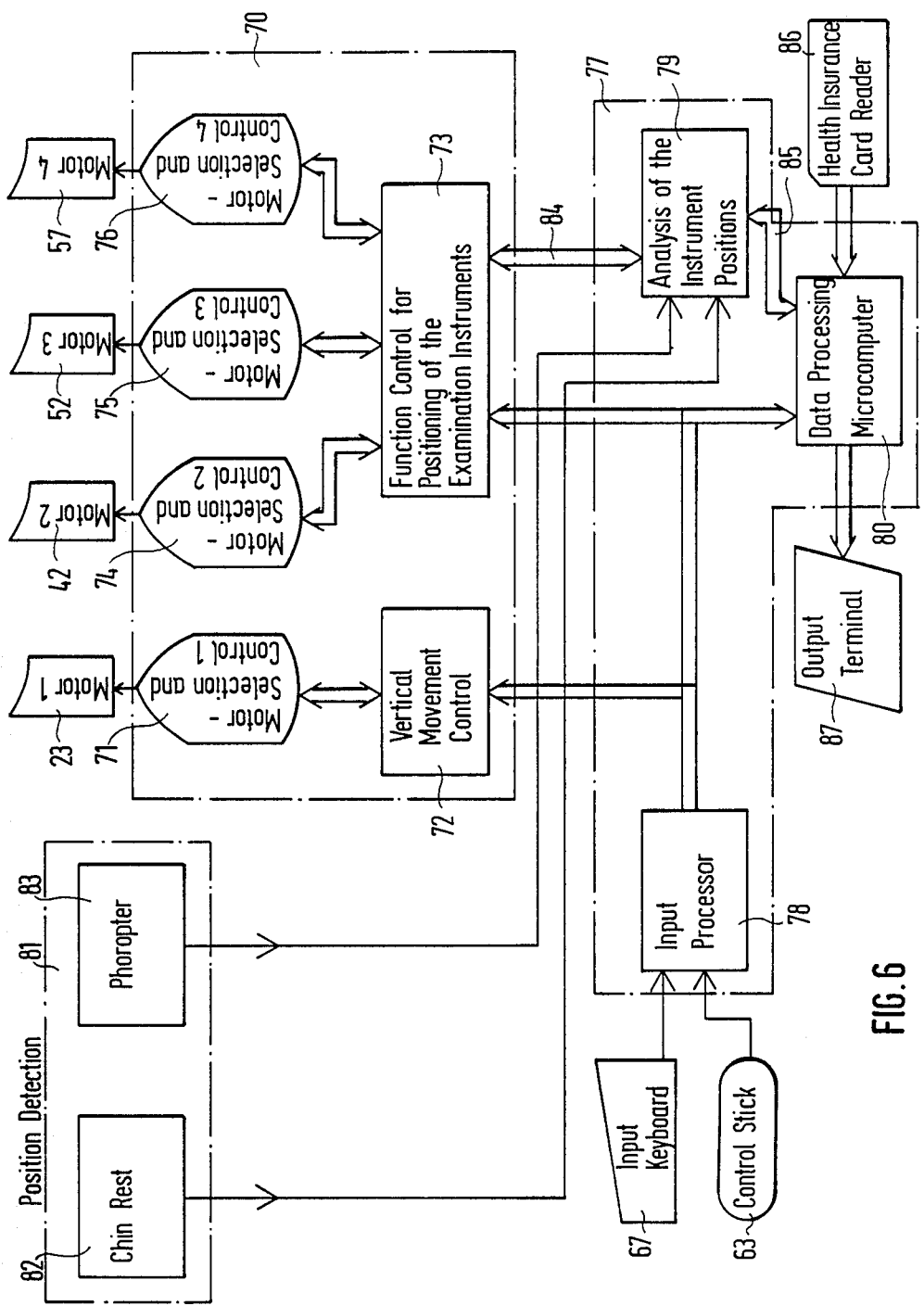
FIG. 6 is a block diagram of an inventive control means of the examination unit according to FIG. 1.

The control element 3 or the base element 2 comprises control means 70 of which a schematic is illustrated in FIG. 6. The control means 70 comprise a control circuitry 72 whose output is connected to a motor selection and control circuitry 71 for the driving motor 23, as well as a process controller 73 whose output is connected respectively to the driving motors 42, 52 and 57 through thre respective motor selection and control circuits 74, 75, 76. The input of hte control means is linked up with a data processing equipment 77 comprising a processor circuitry 78 for the entered data, an analysis circuitry 79 and a microcomputer 80. The input of the processor circuitry 78 is connected to the control switch or control stick 63 as well as the operating elements and controls or the input keyboard 67, while the output is connected to the control circuitry 71, the process controller 73 and the microcomputer. The input of the analysis circuit 79 is connected to position detector means 81 comprising means 82 to detect the position of the chin rest 31, and means 83 to detect the position of the phoropter 30. The term "position" is to denote here the distance by which the chin rest 38 or the phoropter 30 is displaced relative to its rest position by laterally drawing out the telescopic supporst 25, 26. The analysis circuit 79 is also connected through line 84 with the process controller 73 and through line 85 to the microcomputer 80. Finally, one input of the microcomputer is connected to an ID card reader 86 for reading the indentification card of the patient, e.g. the health insurance card, while the output is connected to an output terminal 87, e.g. a printer for the production of a printout on the examination performed.

The position detector means 82, 83 are preferably designed as coding rails attached to the lower mobile rail 29 of the telescopic supports 25, 26, which comprises a coding in correspondence to the displacement of the rail 29, which can be sensed by a detector. Other known distance-sensing means, however, may also be used. In the event that the chin rest 31 or the phoropter 30 will be drawn out for the examination by a predetermined distance, e.g. defined by a stop, the positions of the chin rest 31 and the phoropter 30 may specifically also be sensed through a limit switch. The control switch 63 is designed in the form of a "joystick" to enter the movement in a plurality of directions at the same time. Two speeds can be additionally input through this control switch 63 for each direction of movement and thus for each driving motor 23, 42, 52, 57, i.e. one slow-motion speed or gear for fine adjustment and one quick-motion gear or speed for coarse adjustment.

In operation, the chin rest 31 and the instruments 30, 59, 60 are initially in the pushed-in rest positions shown in FIG. 1. The person to be examined and the examining ophthalmologist take their seats at the side of the examination unit 1 in a manner that the patient to be examined is on one side and the doctor on the other side of the vertical planes containing the displacement paths of the chin rest 31 or the instruments 30,3 49, 60. When, for instance, an examination is to be made with the phoropter 30, this instrument, and together with it the telescopic support 25, is laterally drawn out by hand to an extent that it is positioned in front of the person to be examined. Then the control switch 63 is used to actuate the drive unit 18, first in quick motion and then at slow speed, until the suitable examination elevation of the phoropter 30 is achieved. The position detector 83 senses that the phoropter 30 has been moved into the examining position, and emits a corresponding signal to the data processing equipment 77. This equipment produces a log of the examination, if necessary calculates the fee to be charged with reference to the tariffs, and outputs a voucher or a debit note through the output terminal 87.

When the instruments 59, 60 are to be used for an examination requiring the use of the chin rest 31, first the chin rest 31 is drawn out by hand at the telescopic support 26 and laterally out of the examination unit until it reaches a position on the vertical line through the chin of the person to be examined. The chin rest may, however, also be moved out up to the stop while the chair of the person to be examined is correspondingly aligned. This operating condition is sensed by the position detector 82 and reported to the analysis circuitry 79. Then the control switch 63 is used to actuate the control circuitry 72 and the motor selection and control circuit 71 to control the driving motor 23 or the drive unit 18 until a suitable elevation of the chin rest 31 is reached. The fine adjustment may be achieved at slow motion, if necessary.

The message from the position detector 82 to the analysis circuitry 79 releases the process controller 73 for positioning of the examination instruments 59, 60. The input keyboard 67 may now be used to preselect a certain instrument 59, 60. THis involves the actuation of the displacement drive 56 for the telescopic bracket 53, to which the instruments 59, 60 are fastened, until the selected instrument 59, 60 is displaced into an examination position conforming with the position of the chin rest 31 in the direction of displacement, which is determined by the process controller comparing the displacement distance of the corresponding instrument against the position sensed by the position detector 82. Since the selected instrument 59, 60 has already been vertically moved together with the chin rest 31 for adaptation to the person to be examined, a coarse adjustment of the examination position of the respective instrument has thus been reached.

Now the driving means 37, 48, 56 are actuated for fine adjustment by means of the control stick 63. The fine adjustment of the elevation of the examination instrument is achieved by actuation of the motor 42 of the displacement drive 37 through the motor selector circuitry 74, while the fine adjustment of the spacing between the examination instrument and the chin rest 31 and thus the eyes of the person to be examined is achieved when the motor 52 of the displacement drive 48 is actuated through the motor selector circuitry 75, and the fine adjustment of the lateral alignment of the examination instrument is obtained by selection of the motor 57 of the displacement drive 56 through the motor selector circuitry 76, both through the process controller 73. The motor 57 of the displacement drive 56 is actuated through the control switch 63, too, when the selected examination instrument is to be moved from one eye to the other; for coarse adjustment the quick motion mode may be selected.

When the respective instrument has reached the required examination position the process controller 73 emits a signal to the data processing equipment 77 which, as a response, can then output a voucher or a receipt through the output terminal 87. Moreover, the data can be displayed on the screen 65.

When after the examination using one instrument another examination is to be made with a second instrument, this second instrument is selected through the entry keyboard 67 whereupon the displacement drive 60 56 laterally displaces the telesocpic support by the distance of the two instruments so that the newly selected instrument is moved into the examination position. This movement also involves a coarse adjustment of the second instrument since the elevation of all instruments 59, 60 and their horizontal spacing from the chin rest 31 has already been preset by the aligned mounting at the telescopic bracket 53.

When the examination begins the card input unit 66 may be used to read an ID document, e.g. a health insurance card or an ID card, of the person to be examined into the reader 86. The read data can then be used by the data processing equipment 77 for accounting and can be noted accordingly on the document output on the output terminal 87, for instance.

In order to be able to render the examination independent of the size of the person to be examined, the elevation of the telescopic supports 25, 26, 53 and the suspension of the instruments 30, 31, 59, 60 is so selected that an automatic presetting can be achieved by means of the drive 18 to reach a sighting elevation between 115 and 130 cm, preferably 117.5 to 127.5 cm. The adjustment range for the displacement drive 37 is selected to have $\pm 100$ mm, preferably $\pm 65$ mm, while the adjustment range of the displacement drive is set at $\pm 60$ mm, preferably $\pm 40$ mm, and the lateral adjustment range for the fine adjustment by the displacement drive 56 is selected within the range $\pm 80$ mm, preferably $\pm 50$ mm.

The total lateral displacement distance of the mobile rail 55 and thus the instruments 59, 60, 60' attached thereto, from the rest position, illustrated in broken lines in FIG. 5, into the working position shown with continuous lines is so selected that each of the instruments 59, 60, 60' can be arranged laterally of the instrument assembly at an approximate spacing between 300 and 600 mm, preferably 450 mm. The total lateral displacement distance required is thus determined by he total of this measure and the distance from the center of that instrument 60' which is farthest from the withdrawable end of the rail 55, and that end. When the center distance of the instrument 60' from the withdrawable end of the rail 55 is some 600 mm, for instance, as shown in FIG. 5, the total displacement required is calculated to be $450+600$ mm $=1,050$ mm. Depending on the number and arrangement of the instruments 59, 60, 60' this distance may, however, also have different lengths.

The illustrated structure of the examination unit 1 allows for a stable and vibration-free installation of the instruments 30, 59, 60. Due to the suspended mounting of these instruments, patients of different size can be equally conveinitnely examined. For examination, neither an individual instrument base of the examination instruments nor a vertically adjustable and displaceable chair for the patient are required. The suspended mounting entails the further particular advantage that the space which is normally required for upright installation can be utilized for accomodation and ergonomic arrangement of the operating console, the switchboard, the measuring glasses, the therapeutic element and hand-held instruments and small diagnostic equipment.

The examination instruments 59, 60 are moved into the examination position by electromotors in a common base. The further adjustment, i.e. the vertical, the lateral (from the right to the left eye and vice versa) and the displacement adjustment (focussing relative to the eye) is manually made by means of the control switch 63.

As an alternative, the control switch 63 may also be designed as a foot-operated switch so that the respective instrument can be adjusted to the eye for certain manipulations at the eye which require the use of both hands.

.In a further alternative embodiment, the displacement drive 37 for the bracket frame 36 with the instruments 59, 60 suspended therefrom is supported at the supporting frame 6 instead of the mobile frame 13. This allows for an independent elevation adjustment of the bracket frame 36 and the mobile frame 13 with the chin rest attached thereto. Preferably, however, the drive motor 42 for the elevation adjustment of the bracket frame 36 and the driv emotor 23 for the elevation adjustment of the mobile frame 13 are so controlled that this elevation adjustment of both frames 36, 13 takes place in a defined mutual relationship with a certain switch position, preferably in quick motion, i.e. preferably at the same time and at the same rate. This embodiment, too, has thus the advantage that the instruments 59, 60 are adjusted to the suitable elevation simultaneously with the elevation adjustment of the chin rest 31.

The phoropter for manual or any other operation, which can also be operated through a motor, is also mounted to be withdrawn, and is provided with a tilting articulation for adjustment of the reading angle of inclination.

This leads to the advantage that only one common elevation, lateral and displacement adjustment need be provided for all instruments. Moreover, the inventive examination unit 1 allows for optimum access to the patient while the path of instrument movement does not penetrate into the doctor's or patient's seating space. It also allows for rapid feed and removal of the examination instruments used and requires only little space.

The present invention is not limited to the embodiments described in the foregoing but may rather have numerous modifications and improvements without going beyond the intellectual essence of the invention.

We claim:

1. Ophthalmic examination unit, comprising a common support element having a first cantilever section, said common support element being adjustable in elevation through a first drive, a plurality of examination instruments mounted to said first cantilever section in a suspended arrangement, and a chin rest mounted to said first cantilever section in a suspended arrangement, said common support element having a second cantilever section, additional instruments attached to said second cantilever section, and wherein said second cantilever section is designed for elevation adjustment relative to said first cantilever section by means of a second drive.

2. A unit according to claim 1, wherein said second cantilever section comprises a guide element at which a sliding carriage is guided for displacement substantially in a horizontal and lateral direction, and wherein said additional instruments are attached to said sliding carriage in side-by-side relationship in the direction of displacement.

3. Ophthalmic examination unit, comprising a chin rest and a plurality of examination instruments whose positions can be adjusted by elevation and in lateral direction relative to the eyes to be examined with the chin rest and an instrument being suspended from a common first supporting element and further instruments being suspended from a second supporting element, and with a first drive being provided for elevation adjustment of the first supporting element and a second drive being provided for elevation adjustment of the second supporting element.

4. Unit according to claim 3, wherein said first supporting element comprises a first cantilever section from which said chin rest and said instrument are suspended, and wherein said second supporting element is designed as a cantilver supporting frame from which said further instruments are suspended.

5. Unit according to claim 4, wherein a third drive is provided for adjustment of the spacing between said further instruments and said chin rest, while a fourth drive is provided for lateral movement of said further instruments.

6. Unit according to claim 5, wherein control means are provided which comprise an element to select and control said first drive, said second drive, said third drive and said fourth drive for actuation by the user.

7. Unit according to claim 6, wherein said control means are so designed that one quick-motion and one slow-motion speed can be selected for each drive.

8. Unit according to claim 6, wherein means are provided to detect the position of said chin rest.

9. Unit according to claim 3, wherein said further instruments are attached to said first supporting element through a common foot.

10. Unit according to claim 3, wherein said chin rest is attached to a support guided at said first supporting element for lateral displacement.

11. Unit according to claim 3, wherein a data processing equipment as well as means for the detection of the position of an instrument are provided which emit a signal to the data processing equipment when an instrument is determined to be in the examination position.

12. Unit according to claim 11, comprising an ID card reader connected to the data processing equipment.

13. Unit according to claim 11, wherein the data processing equipment is connected to an output terminal for output of a voucher relative to the examination carried out.

* * * * *